(12) United States Patent
Govari et al.

(10) Patent No.: US 9,005,217 B2
(45) Date of Patent: Apr. 14, 2015

(54) ROBOTIC DRIVE FOR CATHETER

(75) Inventors: Assaf Govari, Haifa (IL); Andres Claudio Altmann, Haifa (IL); Yaron Ephrath, Karkur (IL); Christopher Thomas Beeckler, Brea, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 1246 days.

(21) Appl. No.: 12/539,707

(22) Filed: Aug. 12, 2009

(65) Prior Publication Data

US 2011/0040150 A1    Feb. 17, 2011

(51) Int. Cl.
| | | |
|---|---|---|
| *A61B 1/00* | (2006.01) | |
| *A61B 19/00* | (2006.01) | |
| *A61B 17/00* | (2006.01) | |
| *A61M 25/01* | (2006.01) | |

(52) U.S. Cl.
CPC ....... *A61B 19/2203* (2013.01); *A61B 2017/003* (2013.01); *A61B 2019/2211* (2013.01); *A61M 25/0105* (2013.01); *A61M 25/0113* (2013.01)

(58) Field of Classification Search
CPC ..................... A61M 25/0105; A61M 25/0113; A61M 25/0116; A61B 2019/2211; A61B 19/2203; A61B 2017/003; A61B 2017/22075
USPC ...................... 606/130, 1; 600/424, 117, 146; 604/95.01, 95.04, 510, 528
See application file for complete search history.

(56) References Cited

U.S. PATENT DOCUMENTS

| | | | |
|---|---|---|---|
| 5,391,199 A | 2/1995 | Ben-Haim | |
| 5,754,741 A | 5/1998 | Wang et al. | |
| 5,808,665 A | 9/1998 | Green | |
| 2002/0087151 A1 | 7/2002 | Mody et al. | |
| 2002/0128636 A1 | 9/2002 | Chin et al. | |
| 2004/0133168 A1 | 7/2004 | Salcudean et al. | |
| 2004/0254566 A1 | 12/2004 | Plicchi et al. | |
| 2005/0203382 A1 | 9/2005 | Govari et al. | |
| 2005/0215983 A1* | 9/2005 | Brock ............... | 606/1 |
| 2005/0222554 A1* | 10/2005 | Wallace et al. ........ | 606/1 |

(Continued)

FOREIGN PATENT DOCUMENTS

| | | |
|---|---|---|
| EP | 1915968 A2 | 4/2008 |
| WO | WO 99/45994 A1 | 9/1999 |

(Continued)

OTHER PUBLICATIONS

Chinese Official Action dated May 3, 2013 received from the Chinese Patent Office in related application 201010254196.9 together with English translation.

(Continued)

*Primary Examiner* — Julian W Woo
*Assistant Examiner* — Shaun L David

(57) ABSTRACT

Apparatus for controlling a steerable invasive probe having a handle. The apparatus includes a platform and a jig, which is mounted on the platform and is configured to receive the handle. The jig includes at least a first gear that is positioned and shaped to rotate the handle about an axis of the probe and a second gear that is positioned and shaped to operate a control on the handle for deflecting a tip of the probe. A drive module includes one or more motors. A transmission is coupled to the drive module and to the jig so as to controllably rotate at least the first and second gears and to translate the platform along a direction parallel to the axis in order to advance and retract the probe.

23 Claims, 8 Drawing Sheets

(56) References Cited

U.S. PATENT DOCUMENTS

| | | | |
|---|---|---|---|
| 2006/0229587 A1* | 10/2006 | Beyar et al. | 604/510 |
| 2007/0106147 A1 | 5/2007 | Altmann et al. | |
| 2007/0185486 A1* | 8/2007 | Hauck et al. | 606/41 |
| 2007/0239170 A1* | 10/2007 | Brock et al. | 606/108 |
| 2008/0009791 A1* | 1/2008 | Cohen et al. | 604/95.01 |
| 2008/0033284 A1 | 2/2008 | Hauck | |
| 2008/0140087 A1* | 6/2008 | Barbagli | 606/130 |
| 2009/0024141 A1 | 1/2009 | Stahler | |
| 2009/0105639 A1* | 4/2009 | Weitzner et al. | 604/95.01 |
| 2009/0247943 A1* | 10/2009 | Kirschenman et al. | 604/95.04 |

FOREIGN PATENT DOCUMENTS

| | | |
|---|---|---|
| WO | WO 02/074178 | 9/2002 |
| WO | WO 2009/026351 A1 | 2/2009 |

OTHER PUBLICATIONS

Search Report issued by the People's Republic of China dated Apr. 23, 2013 for corresponding Patent Application No. 201010254196.9.
English-language translation of Japanese Notification of Reasons for Refusal dated Mar. 4, 2014 issued in related Japanese Patent Application No. 2010-180049.

* cited by examiner

ROBOTIC DRIVE FOR CATHETER

FIELD OF THE INVENTION

The present invention relates generally to invasive medical instruments, and specifically to methods and apparatus for manipulating and steering an invasive probe for diagnostic or therapeutic purposes.

BACKGROUND OF THE INVENTION

Various types of robotic steering mechanisms for catheters are known in the art. For example, U.S. Patent Application Publication 2005/0203382, whose disclosure is incorporated herein by reference, describes a robot for steering a catheter that is designed to be manually manipulated by a user. The catheter has a user-operable control handle or a thumb control, and the robot holds and manipulates the catheter by generally mimicking the motions of a hand of a surgeon.

As another example, PCT International Publication WO 99/45994, whose disclosure is incorporated herein by reference, describes a remote control catheterization system including a propelling device, which controllably inserts a flexible, elongate probe into the body of a patient. A control console, in communication with the propelling device, includes user controls which are operated by a user of the system remote from the patient to control insertion of the probe into the body by the propelling device.

SUMMARY OF THE INVENTION

Embodiments of the present invention that are described hereinbelow provide a robotic drive for an invasive medical device, such as a catheter, that enables versatile, precise control of the motion of the device inside the patient's body.

There is therefore provided, in accordance with an embodiment of the present invention, apparatus for controlling a steerable invasive probe having a handle. The apparatus includes a platform and a jig, which is mounted on the platform and is configured to receive the handle. The jig includes at least a first gear that is positioned and shaped to rotate the handle about an axis of the probe and a second gear that is positioned and shaped to operate a control on the handle for deflecting a tip of the probe. A drive module includes one or more motors. A transmission is coupled to the drive module and to the jig so as to controllably rotate at least the first and second gears and to translate the platform along a direction parallel to the axis in order to advance and retract the probe.

In a disclosed embodiment, the second gear is positioned and shaped to rotate a first control wheel for deflecting the tip of the probe in a first direction relative to the axis, and the jig includes a third gear, which is positioned and shaped to rotate a second control wheel on the handle for deflecting the tip of the probe in a second direction, perpendicular to the first direction.

The first and second gears may be configured to encircle the handle.

In some embodiments, the transmission includes at least first and second telescopic drive modules, which are respectively coupled to drive the first and second gears over a range of locations of the platform. Typically, each of the telescopic drive modules includes a driving shaft, which is fixedly coupled to be rotated by a respective motor, and a driven shaft, which is fixedly coupled to the jig so as to move with the platform along the direction parallel to the axis, while slidably engaging the driving shaft so as to be rotated by the driving shaft.

There is also provided, in accordance with an embodiment of the present invention, an invasive medical system, including a steerable invasive probe having an axis and a distal tip for insertion into a body of a subject, and including a handle and at least one control on the handle for controlling a deflection of the distal tip. A robotic drive, includes a platform and a jig, which is mounted on the platform and is configured to receive the handle, and which includes at least a first gear that is positioned and shaped to rotate the handle about the axis of the probe and a second gear that is positioned and shaped to operate the at least one control. A drive module includes one or more motors. A transmission is coupled to the drive module and to the jig so as to controllably rotate at least the first and second gears and to translate the platform along a direction parallel to the axis in order to advance and retract the probe. A control unit is coupled to control the drive module so as to move the probe inside the body.

In a disclosed embodiment, the probe includes a catheter, which is configured for insertion into a heart of the subject.

In some embodiments, the system includes a position-sensing subsystem, for determining position coordinates of the probe inside the body, wherein the control unit is configured to control the drive module responsively to the position coordinates. Typically, the position-sensing subsystem includes a position transducer in the distal tip of the probe.

There is additionally provided, in accordance with an embodiment of the present invention, a method for controlling a steerable invasive probe having a handle. The method includes inserting the handle into a jig, which is mounted on a platform and which includes at least a first gear that is positioned and shaped to rotate the handle about an axis of the probe and a second gear that is positioned and shaped to operate a control on the handle for deflecting a tip of the probe. A transmission is coupled to a drive module, including one or more motors, and to the jig so as to controllably rotate at least the first and second gears and to translate the platform along a direction parallel to the axis in order to advance and retract the probe.

The present invention will be more fully understood from the following detailed description of the embodiments thereof, taken together with the drawings in which:

DETAILED DESCRIPTION OF EMBODIMENTS

Embodiments of the present invention provide a robotic drive that carries out all four types of motion that can normally made by a human operator of a catheter or other steerable probe:
1. In/out (forward/back—advancing the catheter tip farther into the target organ or retracting it outward);
2. Rotation (roll) about the catheter axis;
3. Right/left deflection of the catheter tip;
4. Up/down deflection of the catheter tip.

(For some applications, one direction of deflection is sufficient, since the catheter may be rotated about its axis in order to align the deflection in the desired direction. The second direction of deflection may therefore be considered an additional, optional feature.)

The catheter may be of a standard type, designed for manual control by a human operator, with one or more controls on the handle to control right/left and up/down deflection. In the embodiment pictured below, the controls on the handle have the form of rotatable control wheels, and the robotic jig grips each of these wheels in a gear, and grips the handle itself in another gear. Alternatively, the gears in the jig may be configured to drive controls of other types, such as linear controls.

Each gear is driven by a respective motor via a telescopic transmission shaft assembly ("telescopic" in the sense that the length of the assembly can change during operation). The gears may be driven separately or in concert in order to perform all of the latter three motions in the list above and thus give any desired orientation of the catheter tip. A motorized linear drive moves the entire jig forward and back on a platform to provide in/out motion of the catheter along its axis.

Figure 1:
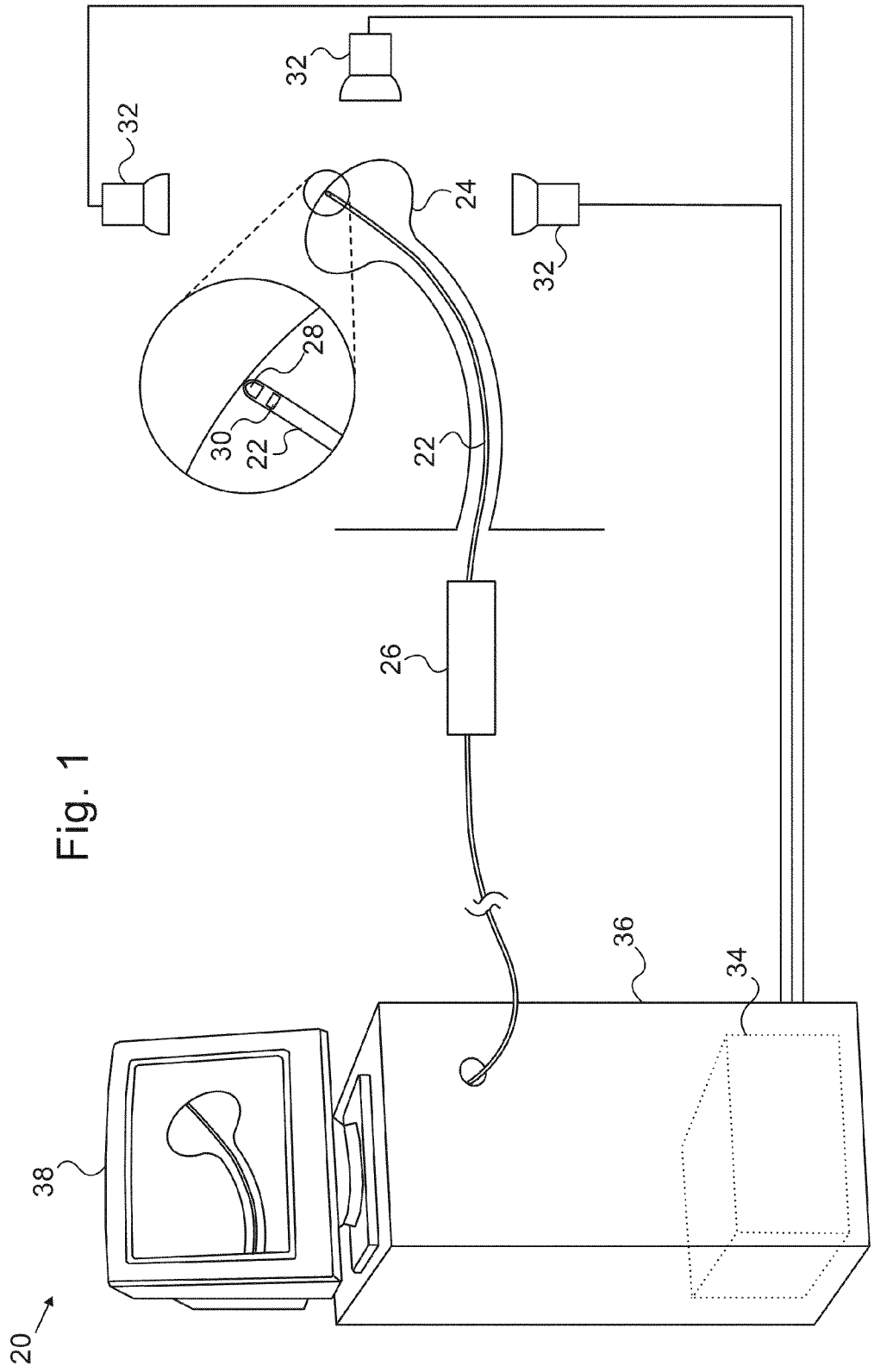
FIG. 1 is a schematic, pictorial illustration of a catheterization system with a robotic drive, in accordance with an embodiment of the present invention.

FIG. 1 is a schematic, pictorial illustration of a catheterization system 20 with a robotic drive 26, in accordance with an embodiment of the present invention. In the illustrated embodiment, a catheter 22 is inserted into a body cavity 24, such as a chamber of the heart of a subject. The distal tip of the catheter (shown enlarged in the inset) typically comprises a functional element 28 for diagnostic and/or therapeutic purposes. For example, element 28 may comprise an electrode for electrical sensing and/or ablation of tissue, or an ultrasonic transducer for intracardiac imaging. Other types of functional elements and invasive probes that may be driven in the manner described below will be apparent to those skilled in the art and are considered to be within the scope of the present invention.

In the pictured embodiment, catheter 22 also comprises a position transducer 30 within its distal tip, for use in determining position coordinates of the tip. For example, transducer 30 may comprise a magnetic field sensor, which detects magnetic fields generated by field transducers 32 at known locations outside the body. Magnetic position sensing systems of this sort are described, for example, in U.S. Pat. No. 5,391,199, whose disclosure is incorporated herein by reference, and are used in intracardiac tracking systems, such as CARTO™ (produced by Biosense Webster Inc., Diamond Bar, Calif.). Alternatively, transducer 30 may generate fields to be sensed by transducers 32. Further alternatively or additionally, transducer 30 may comprise any other suitable type of position transducer known in the art, such as an electrode for purposes of impedance-based position sensing, an ultrasonic transducer, or a fiducial mark for locating the catheter tip in a two- or three-dimensional image of the body.

A position-sensing module 34 communicates with transducers 30 and 32 in order to determine the position coordinates of the catheter tip inside the body of the subject. A control unit 36 uses the coordinates to control drive 26 in order to navigate catheter 22 to desired positions within the body. In this respect, control unit 36 may operate autonomously, in accordance with predefined program instructions. Alternatively or additionally, the control unit may present the catheter position on a display 38, typically juxtaposed on a map or image of cavity 24, so as to enable a human operator (not shown) to control the catheter. Control unit 36 typically comprises a general-purpose computer processor, which is programmed in software to carry out the desired functions.

Figure 2:
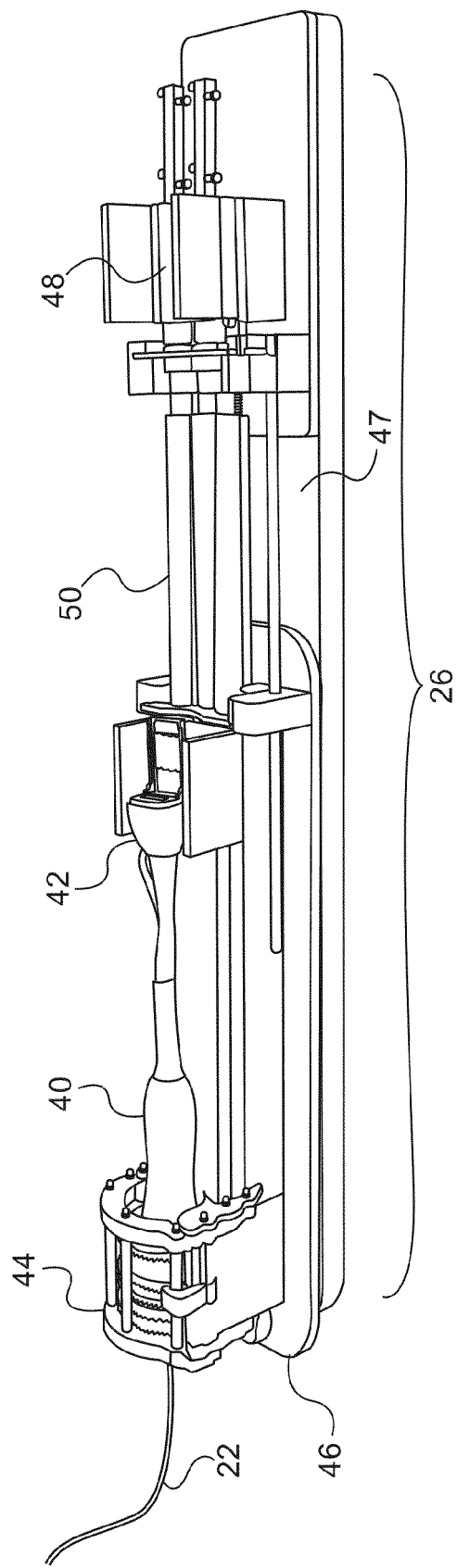
FIG. 2 is a schematic, pictorial illustration showing a catheter held in a robotic drive, in accordance with an embodiment of the present invention.

FIG. 2 is a schematic, pictorial illustration showing catheter 22 held in robotic drive 26, in accordance with an embodiment of the present invention. Catheter 22 comprises a handle 40, which is designed to be held and manipulated by a human operator. In conventional use, the operator inserts the distal end of the catheter percutaneously into a blood vessel, and then advances the catheter along its longitudinal axis through the blood vessel into cavity 24. The operator uses two control wheels on handle 40 (shown below in FIG. 5B) to deflect the distal end of the catheter in respective, mutually-perpendicular directions relative to the catheter axis. The operator moves the handle back and forth in order to advance and retract the catheter, and may also rotate the handle about the axis in order to rotate the catheter itself. A proximal terminal 42 connects the catheter to control unit 36, but this connection is omitted from FIG. 2 for the sake of simplicity and clarity of illustration.

In the present embodiment, however, drive 26 carries out these manipulations instead of the human operator. A jig 44 holds handle 40. The jig comprises one gear (or set of gears) for rotating the handle about the axis and other gears for rotating the control wheels on the handle (as shown below in FIGS. 4 and 5A). Jig 44 is mounted on a platform 46, which is capable of translating relative to a base 47 in order to advance and retract the catheter along its axis. A drive module 48 is coupled by a transmission 50 to jig 44 in order to rotate the gears and to translate platform 46 along base 47. The components of the jig and drive module are shown in greater detail in the figures that follow.

Figure 3A:
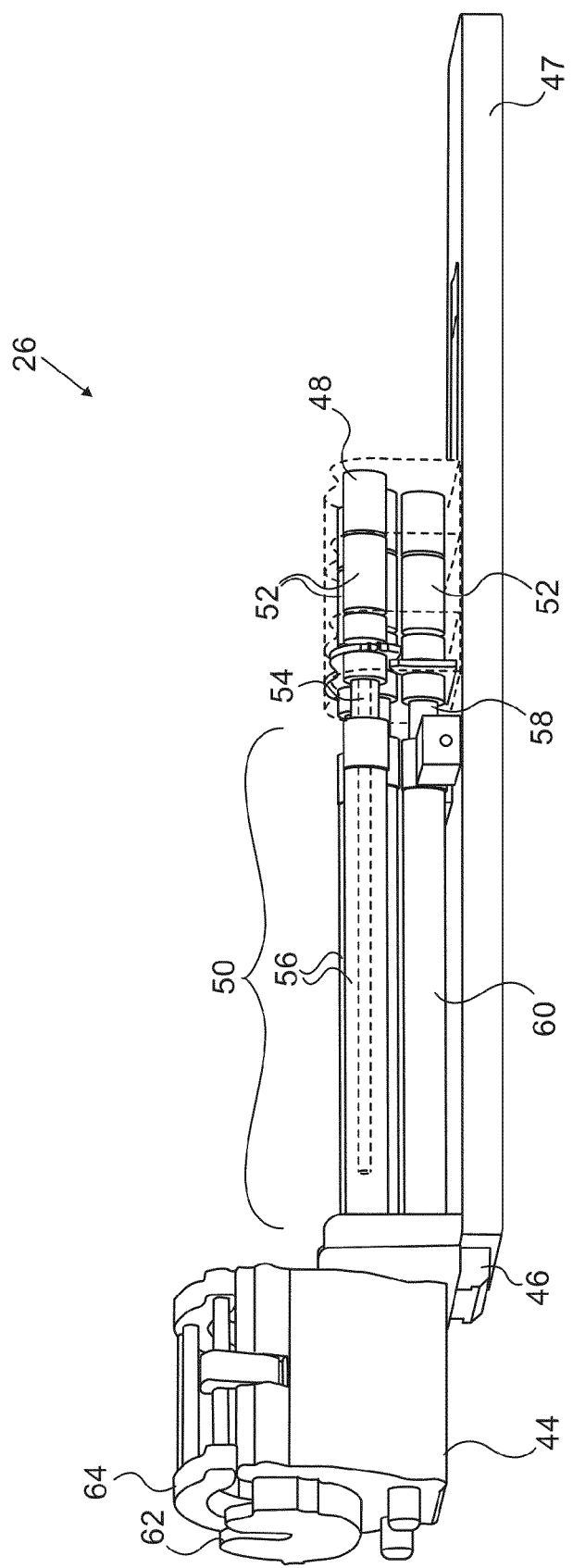
FIGS. 3A and 3B are schematic side and top views, respectively, of a robotic drive for a catheter, in accordance with an embodiment of the present invention.
Figure 3B:
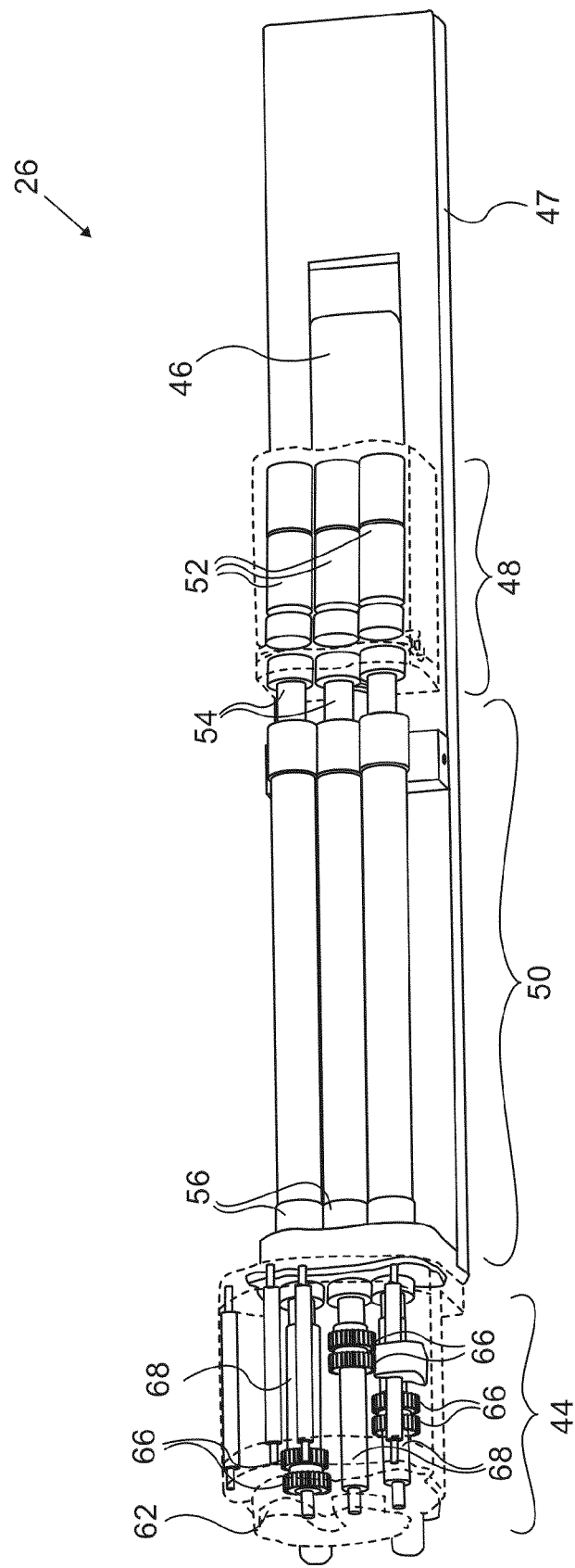

FIGS. 3A and 3B are schematic side and top views, respectively, of robotic drive 26, in accordance with an embodiment of the present invention. Drive module 48 comprises four electric motors 52, such as miniature stepper or servo motors, which are controlled by control unit 36 (FIG. 1). In this embodiment, the lower motor (in the view seen in FIG. 3A) is connected by a linear drive 58 to advance and retract a shaft 60. As this shaft advances or retracts, it moves platform 46 relative to base 47, and thus advances or retracts jig 44 and catheter 22. In this manner, catheter 22 is advanced and retracted inside the subject's body.

The three upper motors 52 are coupled to telescopic drive modules, each comprising a driving shaft 54 and a driven shaft 56. The driving shaft is fixedly coupled to be rotated by the respective motor, while the driven shaft is fixedly coupled to jig 44 so as to move with platform 46 while slidably engaging the driving shaft. This telescopic arrangement, which is shown in greater detail in FIGS. 6A and 6B, enables driven shafts 56 to be rotated by driving shafts 54 over a large range of longitudinal positions of the platform.

Figure 4:
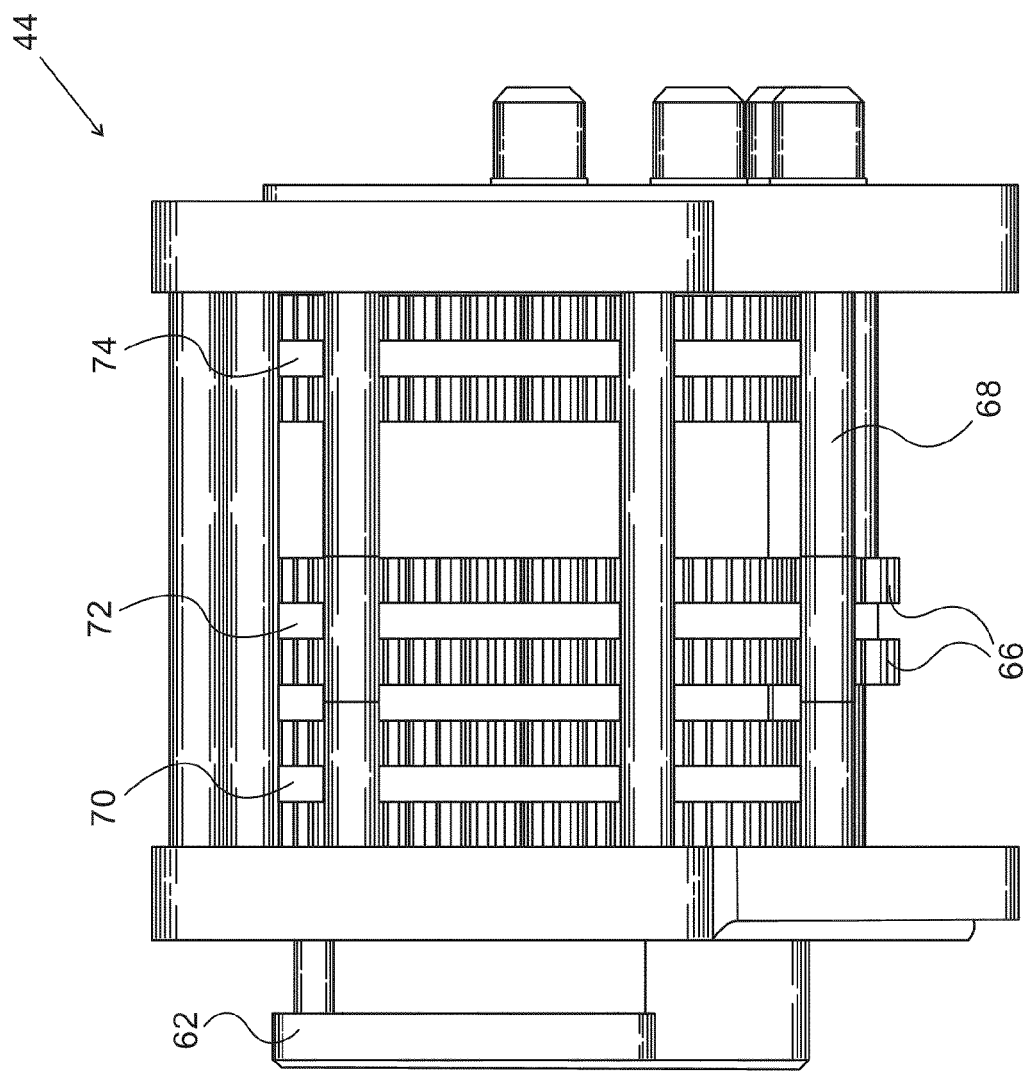
FIG. 4 is a schematic side view of a jig used to grip a catheter in a robotic drive, in accordance with an embodiment of the present invention.

As noted above, jig 44 holds handle 40 of catheter 22, while the catheter itself protrudes out through a collar 62. After the handle is inserted into the jig, a cover 64 encloses and secures the handle in place. The handle is encircled by gears (shown in the figures that follow), which are driven by gears 66 on shafts 68. These shafts are respectively connected to rotate as continuations of driven shafts 56. In the pictured embodiment, each shaft 68 has a pair of gears 66 for more FIG. 4 is a schematic side view of jig 44, in accordance with an embodiment of the present invention. This figure shows gears 70, 72 and 74, which encircle the catheter handle (not shown in this figure) and are able to rotate freely within jig 44. Each of gears 70, 72 and 74 is rotated by one of gears 66 on a respective shaft 68. The longitudinal position of each of gears 66 determines which one of gears 70, 72 and 74 it will rotate.

Figure 5A:
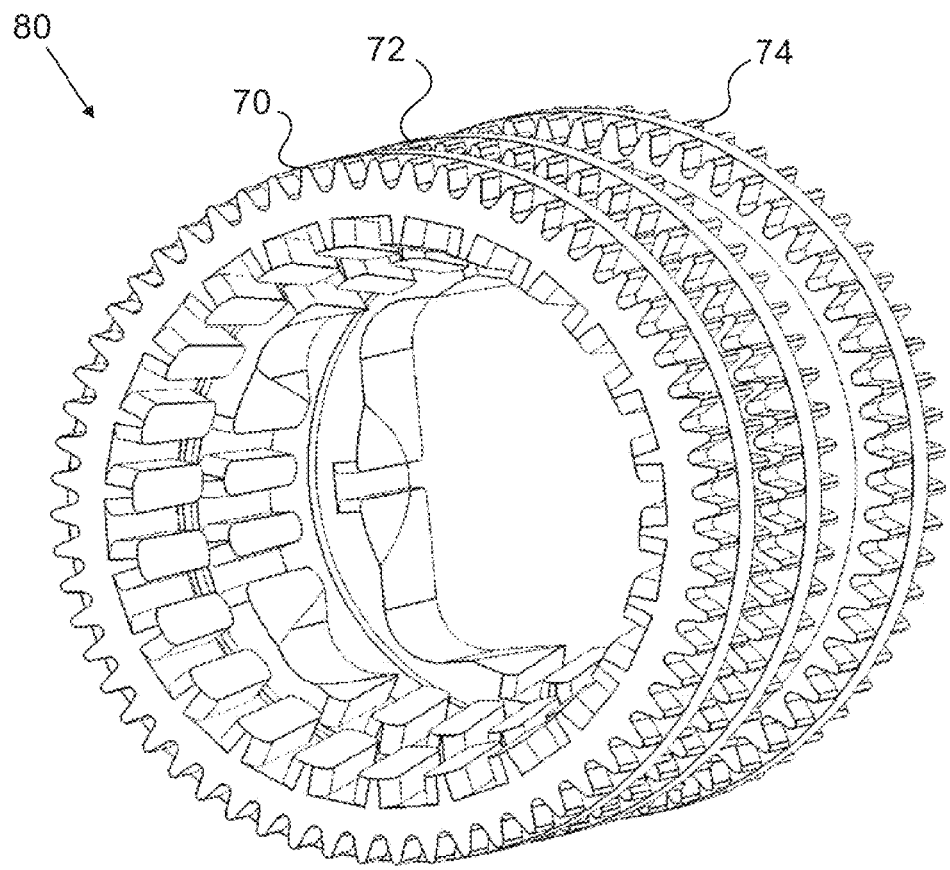
FIG. 5A is a schematic, pictorial illustration of a set of gears used in controlling a catheter, in accordance with an embodiment of the present invention.
Figure 5B:
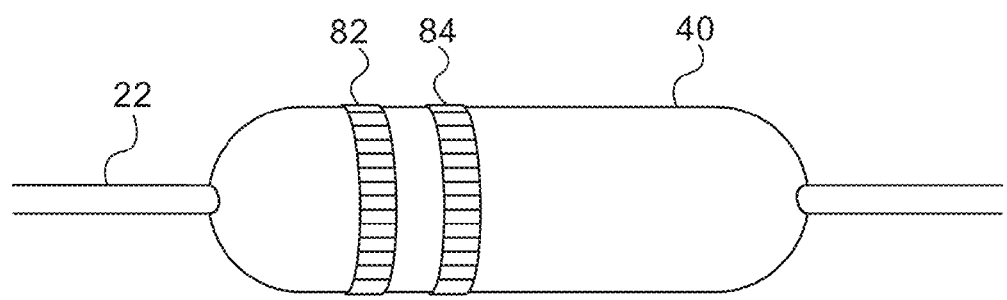
FIG. 5B is a schematic side view of a catheter handle including rotary controls that are engaged by the gears of FIG. 5A in accordance with an embodiment of the present invention.

Reference is now made to FIGS. 5A and 5B, which show further details of the manner of operation of jig 44, in accordance with an embodiment of the present invention. FIG. 5A is a schematic, pictorial illustration of a set 80 of gears 70, 72 and 74. FIG. 5B is a schematic side view of catheter handle 40, including control wheels 82 and 84, which are engaged by gears 70 and 72. Rotating each of these control wheels deflects the distal tip of catheter 22 in a respective direction. (Both control wheels may be rotated together to give a diagonal deflection.)

In preparation for operation of drive 26, gears 70, 72 and 74 are slid over handle 40 so that gear 70 encircles and grasps wheel 82, while gear 72 encircles and grasps wheel 84. Gear 74 holds handle 40 itself, and the internal shape of this gear is, in this example, squared off in order to maintain a firm grip on the handle. Gears 70, 72 and 74 rotate independently, under control of driving gears 66, in order to enable drive 26 to rotate and deflect catheter 22 to any desired orientation.

Figure 6A:
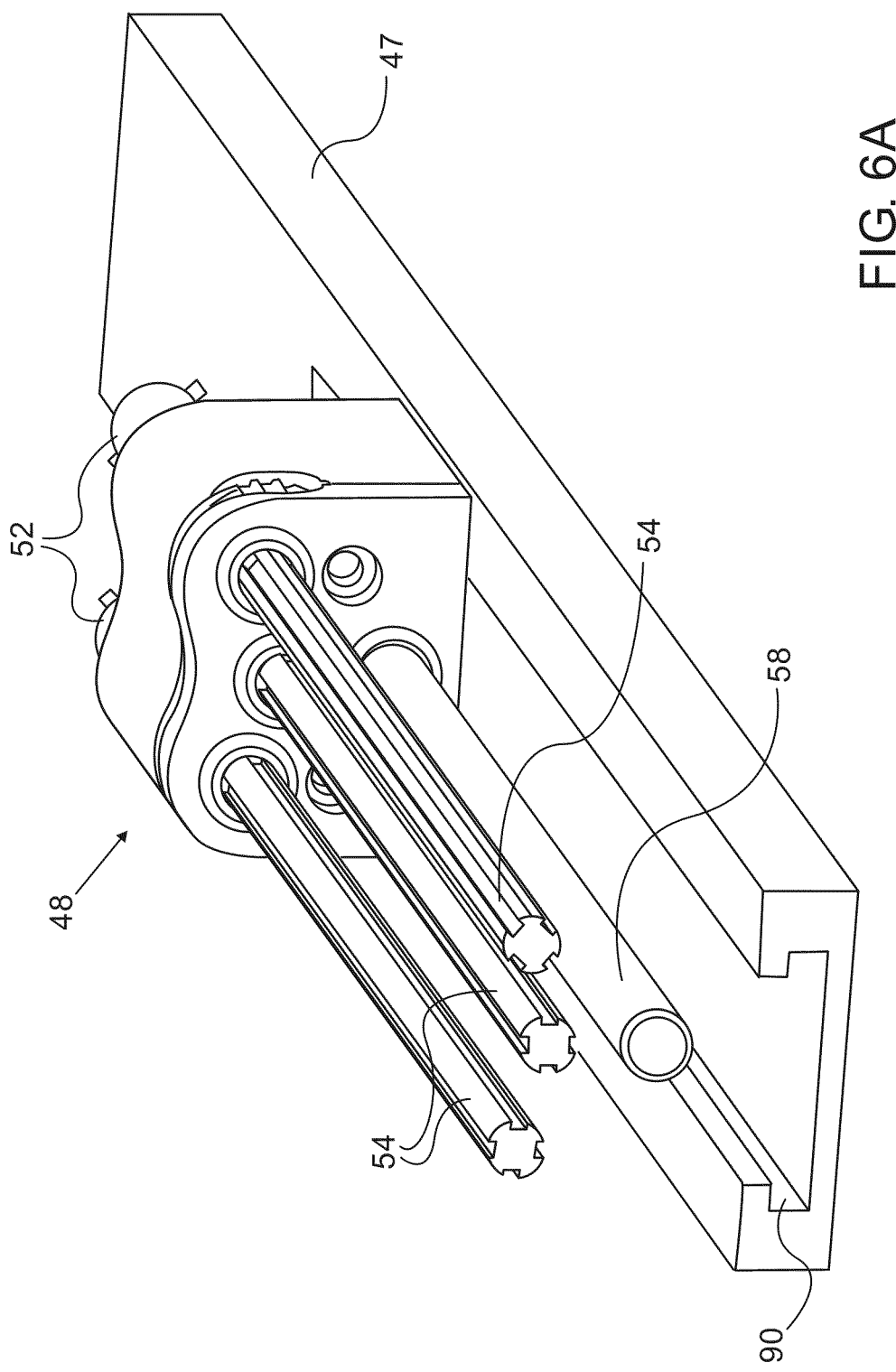
FIGS. 6A and 6B are schematic, pictorial illustrations of driving and driven subassemblies, respectively, of a transmission used in driving a catheter, in accordance with an embodiment of the present invention.
Figure 6B:
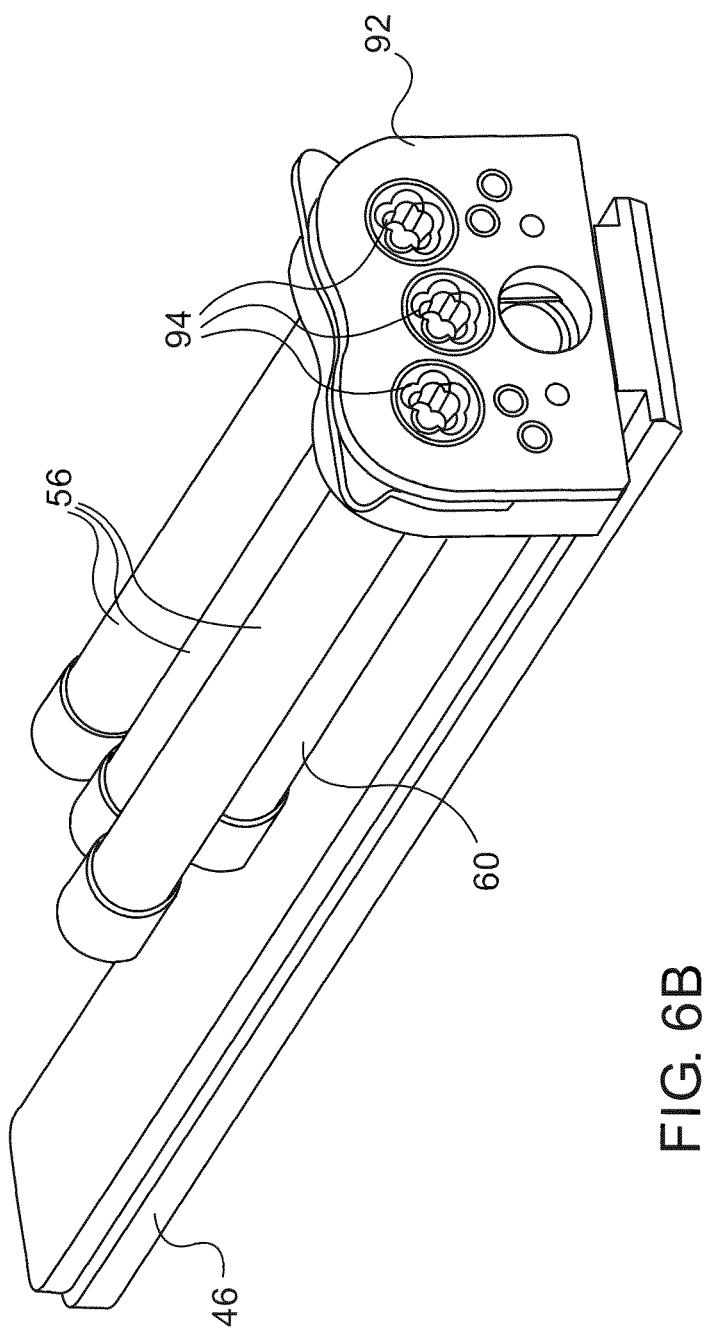

FIGS. 6A and 6B are schematic, pictorial illustrations of driving and driven subassemblies, respectively, of a transmission used in driving a catheter, in accordance with an embodiment of the present invention. The driving subassembly, shown in FIG. 6A, comprises driving shafts 54 and linear drive 58, which are fixedly connected to respective motors 52 in drive module 48. Shafts 54 have an irregular (not circularly-symmetrical) cross-sectional profile. Drive module 48 is mounted on base 47, which contains a track 90 for receiving platform 46.

The driven subassembly, shown in FIG. 6B, is mounted on platform 46 and thus translates longitudinally relative to the driving subassembly. The subassemblies are coupled to one another by a coupling subassembly 92, which contains nuts 94 attached to respective driven shafts 56. Nuts 94 are shaped to match the profiles of driving shafts 54, which will thus slide in and out telescopically through the nuts as platform 46 moves back and forth in track 90. Rotation of driving shafts 54, however, will drive concomitant rotation of driven shafts 56, regardless of the relative longitudinal locations of the shafts. Thus, drive 26 maintains consistent control of the orientation of catheter 22 as the catheter is advanced into and retracted from the body.

Drive mechanisms of the type described above can be used to drive two catheters to operate at the same time. For example, one of the catheters may be used for a therapeutic purpose, such as ablation treatment, while the other captures ultrasonic images of the therapeutic catheter. An application of this sort is described in U.S. Patent Application Publication 2007/0106147, whose disclosure is incorporated herein by reference: The ultrasound catheter is controlled robotically to ensure that the catheter is pointed toward the appropriate target, such as the therapeutic catheter. The position sensing system determines the direction in which the catheter should be pointed and measures any deviations from this direction, using a magnetic position sensor in the catheter. It then corrects the catheter position and orientation automatically, using the robotic drive mechanism, to keep the therapeutic catheter in its field of view.

Although the above embodiments relate, for the sake of clarity of explanation, specifically to catheter 22, the principles of the present invention may similarly be applied to other types of steerable invasive probes, such as endoscopes. The specific shapes and configurations of the components of drive 26 that are shown in the figures are adapted for the specific shape and properties of the catheter. Alternative configurations, for achieving similar functionality in connection with catheter 22 or with other types of invasive probes, will be apparent to those skilled in the art on the basis of the above description and are considered to be within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for controlling a steerable invasive probe having a handle, the apparatus comprising:
   a platform;
   a jig having an internal cavity formed in a body of the jig, the jig being mounted on the platform and configured to receive the handle, and which comprises at least a first gear that is positioned within the internal cavity of the jig and shaped to rotate the handle about an axis of the probe and a second gear that is positioned within the internal cavity of the jig and shaped to operate a control on the handle for deflecting a tip of the probe;
   a drive module comprising at least first and second motors coupled to the first and second gears, respectively; and
   a transmission coupled to the drive module and to the jig, the transmission comprising at least first and second telescopic drive mechanisms configured to controllably rotate at least the first and second gears, a linear drive mechanism configured to translate the platform along a direction parallel to the axis in order to advance and retract the probe, and a coupling subassembly configured to mechanically couple the at least first and second telescopic drive mechanisms and the linear drive mechanism to the drive module.

2. The apparatus according to claim 1, wherein the second gear is positioned and shaped to rotate a first control wheel for deflecting the tip of the probe in a first direction relative to the axis, and wherein the jig comprises a third gear, which is positioned and shaped to rotate a second control wheel on the handle for deflecting the tip of the probe in a second direction, perpendicular to the first direction.

3. The apparatus according to claim 1, wherein the first and second gears are configured to encircle the handle.

4. The apparatus according to claim 1, wherein the at least first and second telescopic drive mechanisms are respectively coupled to drive the first and second gears over a range of locations of the platform.

5. The apparatus according to claim 4, wherein each of the telescopic drive mechanisms comprises:
   a driving shaft, which is fixedly coupled to be rotated by a respective motor; and
   a driven shaft, which is fixedly coupled to the jig so as to move with the platform along the direction parallel to the axis, while slidably engaging the driving shaft so as to be rotated by the driving shaft.

6. The apparatus according to claim 5, wherein the transmission comprises a linear drive mechanism which comprises a linear drive fixedly coupled to be translated by a respective motor and a linear shaft which is fixedly connected to the jig so as to translate the jig along the direction parallel to the axis of the probe.

7. The apparatus according to claim 1, and comprising a control unit, which comprises a position-sensing module, for determining position coordinates of the probe inside a body of a subject, and which is coupled to control the drive module so as to move the probe inside the body responsively to the position coordinates.

8. An invasive medical system, comprising:
   a steerable invasive probe having an axis and a distal tip for insertion into a body of a subject, and comprising a handle and at least one control on the handle for controlling a deflection of the distal tip;
   a robotic drive, comprising:
      a platform;
      a jig having an internal cavity formed in a body of the jig, the jig being mounted on the platform and is configured to receive the handle, and which comprises at least a first gear that is positioned within the internal cavity of the jig and shaped to rotate the handle about the axis of the probe and a second gear that is positioned within the internal cavity of the jig and shaped to operate the at least one control;
      a drive module comprising at least first and second motors coupled to the first and second gears, respectively; and
      a transmission coupled to the drive module and to the jig, the transmission comprising at least first and second telescopic drive mechanisms configured to controllably rotate at least the first and second gears, a linear drive mechanism configured to translate the platform along a direction parallel to the axis in order to advance and retract the probe, and a coupling subassembly configured to mechanically couple the at least first and second telescopic drive mechanisms and the linear drive mechanism to the drive module; and
   a control unit, which is coupled to control the drive module so as to move the probe inside the body.

9. The system according to claim 8, wherein the probe comprises a catheter, which is configured for insertion into a heart of the subject.

10. The system according to claim 8, a comprising a position-sensing subsystem, for determining position coordinates of the probe inside the body, wherein the control unit is configured to control the drive module responsively to the position coordinates.

11. The system according to claim 9, wherein the position-sensing subsystem comprises a position transducer in the distal tip of the probe.

12. The system according to claim 8, wherein the second gear is positioned and shaped to rotate a first control wheel for deflecting the tip of the probe in a first direction relative to the axis, and wherein the jig comprises a third gear, which is positioned and shaped to rotate a second control wheel on the handle for deflecting the tip of the probe in a second direction, perpendicular to the first direction.

13. The system according to claim 8, wherein the first and second gears are configured to encircle the handle.

14. The system according to claim 8, wherein the at least first and second telescopic drive mechanisms are respectively coupled to drive the first and second gears over a range of locations of the platform.

15. The system according to claim 14, wherein each of the telescopic drive mechanisms comprises:
   a driving shaft, which is fixedly coupled to be rotated by a respective motor; and
   a driven shaft, which is fixedly coupled to the jig so as to move with the platform along the direction parallel to the axis, while slidably engaging the driving shaft so as to be rotated by the driving shaft.

16. A method for controlling a steerable invasive probe having a handle, the method comprising:
   inserting the handle into an internal cavity of a jig, which is mounted on a platform and which comprises at least a first gear that is positioned within the internal cavity of the jig and shaped to rotate the handle about an axis of the probe and a second gear that is positioned within the internal cavity of the jig and shaped to operate a control on the handle for deflecting a tip of the probe; and
   mechanically coupling, by a coupling subassembly, a transmission to a drive module comprising at least first and second motors coupled to the first and second gears respectively, and to the jig, controlling at least first and second telescopic drive mechanisms to rotate at least the first and second gears, and controlling a linear drive mechanism to translate the platform along a direction parallel to the axis in order to advance and retract the probe.

17. The method according to claim 16, wherein the probe comprises a catheter, and wherein the method comprises inserting the catheter into a heart of a subject, and operating the drive module so as to navigate the catheter in the heart.

18. The method according to claim 16, comprising determining position coordinates of the probe inside the body using a position-sensing subsystem, and controlling the drive module responsively to the position coordinates.

19. The method according to claim 18, wherein the position-sensing subsystem comprises a position transducer in a distal tip of the probe.

20. The method according to claim 16, wherein the second gear is positioned and shaped to rotate a first control wheel for deflecting the tip of the probe in a first direction relative to the axis, and wherein the jig comprises a third gear, which is positioned and shaped to rotate a second control wheel on the handle for deflecting the tip of the probe in a second direction, perpendicular to the first direction.

21. The method according to claim 16, wherein the first and second gears encircle the handle.

22. The method according to claim 16, wherein the transmission at least first and second telescopic drive mechanisms are respectively coupled to drive the first and second gears over a range of locations of the platform.

23. The method according to claim 21, wherein each of the telescopic drive mechanisms comprises:
   a driving shaft, which is fixedly coupled to be rotated by a respective motor; and
   a driven shaft, which is fixedly coupled to the jig so as to move with the platform along the direction parallel to the axis, while slidably engaging the driving shaft so as to be rotated by the driving shaft.

* * * * *